(12) United States Patent
Matthews et al.

(10) Patent No.: US 7,674,906 B2
(45) Date of Patent: Mar. 9, 2010

(54) TETRACYCLIC IMMUNOMODULATORY COMPOUNDS

(75) Inventors: Ian Richard Matthews, Oxfordshire (GB); Philip Huxley, Oxfordshire (GB); Filippo Magaraci, Oxfordshire (GB); Chris James Brennan, Oxfordshire (GB); Muhammed Kamal Uddin, Oxfordshire (GB); Lars Olof Göran Pettersson, Lund (SE); Dorthe da Graca Thrige, Lund (SE)

(73) Assignee: Active Biotech AB, Lund (SE)

( * ) Notice: Subject to any disclaimer, the term of this patent is extended or adjusted under 35 U.S.C. 154(b) by 1102 days.

(21) Appl. No.: 10/537,538

(22) PCT Filed: Dec. 12, 2003

(86) PCT No.: PCT/SE03/01941

§ 371 (c)(1),
(2), (4) Date: Sep. 15, 2005

(87) PCT Pub. No.: WO2004/055014

PCT Pub. Date: Jul. 1, 2004

(65) Prior Publication Data

US 2006/0035919 A1 Feb. 16, 2006

Related U.S. Application Data

(60) Provisional application No. 60/433,580, filed on Dec. 16, 2002.

(30) Foreign Application Priority Data

Dec. 16, 2002 (SE) .................... 0203722

(51) Int. Cl.
C07D 471/04 (2006.01)
A61K 31/437 (2006.01)
(52) U.S. Cl. ........................ 546/82; 514/293
(58) Field of Classification Search .................. 546/82
See application file for complete search history.

(56) References Cited

U.S. PATENT DOCUMENTS

| 6,642,249 B2 * | 11/2003 | Bjork et al. ................. 514/293 |
| 7,081,456 B2 * | 7/2006 | Matthews et al. ...... 514/212.08 |
| 7,291,612 B2 * | 11/2007 | Matthews et al. ...... 514/212.08 |

FOREIGN PATENT DOCUMENTS

| EP | 0 354 693 | | 2/1990 |
| WO | WO 91/11448 | * | 8/1991 |
| WO | WO 97/34893 | | 9/1997 |
| WO | WO 03/004495 | | 1/2003 |

* cited by examiner

*Primary Examiner*—Rita J Desai
(74) *Attorney, Agent, or Firm*—Buchanan Ingersoll & Rooney PC

(57) ABSTRACT

The present invention relates to novel heterocyclic compounds, to methods for their preparation, to compositions containing them, and to methods and use for clinical treatment of medical conditions which may benefit from immunomodulation, including rheumatoid arthritis, multiple sclerosis, diabetes, asthma, transplantation, systemic lupus erythematosis and psoriasis. More particularly, the present invention relates to novel heterocyclic compounds, which are CD80 antagonists capable of inhibiting the interactions between CD80 and CD28.

16 Claims, No Drawings

TETRACYCLIC IMMUNOMODULATORY COMPOUNDS

This is a filing under 35 U.S.C. § 371 of International Application No. PCT/SE2003/001941, filed Dec. 12, 2003 that designates the United States of America, and the benefit is claimed under 35 U.S.C. § 119(a)-(d) of Swedish Application No. 0203722-4, filed Dec. 16, 2002, and under 35 U.S.C. § 119(e) of U.S. Provisional Application No. 60/433,580, filed Dec. 16, 2002.

The present invention relates to novel heterocyclic compounds, to methods for their preparation, to compositions containing them, and to methods and use for clinical treatment of medical conditions which may benefit from immunomodulation, including rheumatoid arthritis, multiple sclerosis, diabetes, asthma, transplantation, systemic lupus erythematosis and psoriasis. More particularly the present invention relates to novel heterocyclic compounds, which are CD80 antagonists capable of inhibiting the interactions between CD80 and CD28.

BACKGROUND OF THE INVENTION

The immune system possesses the ability to control the homeostasis between the activation and inactivation of lymphocytes through various regulatory mechanisms during and after an immune response. Among these are mechanisms that specifically inhibit and/or turn off an immune response. Thus, when an antigen is presented by MHC molecules to the T-cell receptor, the T-cells become properly activated only in the presence of additional co-stimulatory signals. In the absence of accessory signals there is no lymphocyte activation and either a state of functional inactivation termed anergy or tolerance is induced, or the T-cell is specifically deleted by apoptosis.

One such co-stimulatory signal involves interaction of CD80 on specialised antigen-presenting cells with CD28 on T-cells, which has been demonstrated to be essential for full T-cell activation. (Lenschow et al. (1996) Annu. Rev. Immunol., 14, 233-258)

A paper by Erbe et al, in J. Biol. Chem. Vol. 277, No. 9, pp 7363-7368, describes three small molecule ligands which bind to CD80, and inhibit binding of CD80 to CD28 and CTLA4. Two of the disclosed ligands are fused pyrazolones of structures A and B:

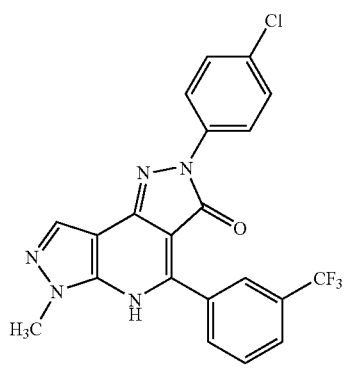

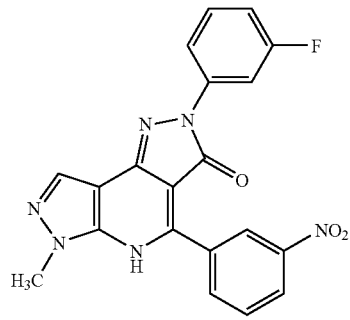

Compound C is disclosed in U.S. Pat. No. 4,312,870 as one of several psychoactive compounds but without biological data. Some related compounds are described by A. Carotti in Bioorganic & Medicinal Chemistry 6 (1998) 389-399, and from their data it is obvious that the carboxylic acid substituent greatly diminishes biologic activity measured as affinity for the CNS benzodiazepine receptor.

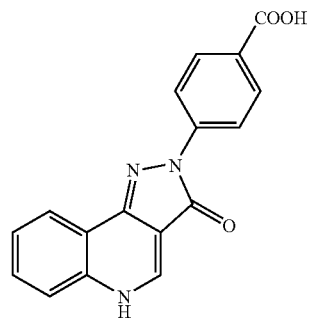

EP 0354693A1 (Boots) discloses immunomodulatory compounds of general structure D but does not include structures wherein R7 and/or R8 are COOH or contain a COOH group.

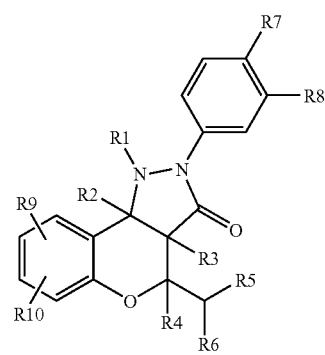

Similarly EP 0354694A1 (Boots) discloses immunomodulatory compounds of general structure E but here are not included structures wherein R6 and/or R7 are COOH or contain a COOH group.

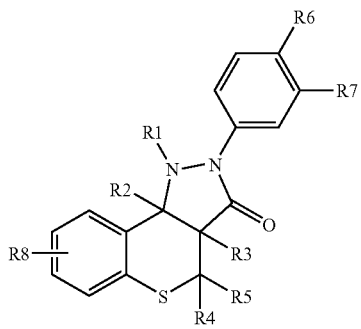

Also, WO9111448 (Boots) discloses immunomodulatory compounds of general structure F but here are not included structures wherein R7 and/or R8 and R8' are COOH or contain a COOH group.

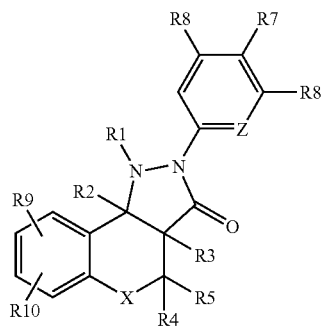

DESCRIPTION OF THE INVENTION

According to the present invention there is provided a compound of formula (I) or a pharmaceutically or veterinarily acceptable salt thereof:

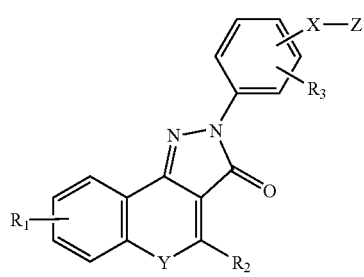

wherein

Z represents a carboxylic acid group (—COOH) or an ester thereof;

$R_1$ and $R_3$ independently represent H; F; Cl; Br; —$NO_2$; —CN; $C_1$-$C_6$ alkyl optionally substituted by F or Cl; or $C_1$-$C_6$ alkoxy optionally substituted by F;

$R_2$ represents optionally substituted $C_3$-$C_7$ cycloalkyl or optionally substituted phenyl;

Y represents —O—, —S—, N-oxide, or —N($R_5$)— wherein $R_5$ represents H or $C_1$-$C_6$ alkyl;

X represents a bond or a group selected from; a divalent $C_1$-$C_6$ alkylene radical, NHC(O) $C_{1-5}$ alkyl, NHC(O) $CH_2$—O—$CH_2$ or C(O)—NH— (amino acid residue);

Compounds of general formula (I) are CD80 antagonists. They inhibit the interaction between CD80 and CD28 and thus the activation of T cells, thereby modulating the immune response.

Accordingly the invention also includes:

(i) a compound of formula (I) or a pharmaceutically or veterinarily acceptable salt thereof for use in the treatment of conditions which benefit from immunomodulation.

(ii) the use of a compound of formula (I) or a pharmaceutically or veterinarily acceptable salt thereof in the manufacture of a medicament for the treatment of conditions which benefit from immunomodulation.

(iii) a method of immunomodulation in mammals, including humans, comprising administration to a mammal in need of such treatment an immunomodulatory effective dose of a compound of formula (I) or a pharmaceutically or veterinarily acceptable salt thereof.

(iv) a pharmaceutical or veterinary composition comprising a compound of formula (I) or a pharmaceutically or veterinarily acceptable salt thereof together with a pharmaceutically or veterinarily acceptable excipient or carrier.

Conditions which benefit from immunomodulation include:

Acute disseminated encephalomyelitis
Adrenal insufficiency
Allergic angiitis and granulomatosis
Amylodosis
Ankylosing spondylitis
Asthma
Autoimmune Addison's disease
Autoimmune alopecia
Autoimmune chronic active hepatitis
Autoimmune hemolytic anemia
Autoimmune neutropenia
Autoimmune thrombocytopenic purpura
Behcet's disease
Cerebellar degeneration
Chronic active hepatitis
Chronic inflammatory demyelinating polyradiculoneuropathy
Chronic neuropathy with monoclonal gammopathy
Classic polyarteritis nodosa
Congenital adrenal hyperplasia
Cryopathies
Dermatitis herpetiformis
Diabetes
Eaton-Lambert myasthenic syndrome
Encephalomyelitis
Epidermolysis bullosa acquisita
Erythema nodosa
Gluten-sensitive enteropathy
Goodpasture's syndrome
Guillain-Barre syndrome
Hashimoto's thyroiditis
Hyperthyrodism
Idiopathic hemachromatosis
Idiopathic membranous glomerulonephritis
Isolated vasculitis of the central nervous system
Kawasaki's disease
Minimal change renal disease
Miscellaneous vasculitides
Mixed connective tissue disease
Multifocal motor neuropathy with conduction block
Multiple sclerosis Myasthenia gravis
Opsoclonus-myoclonus syndrome
Pemphigoid
Pemphigus
pernicious anemia
Polymyositis/dermatomyositis
Post-infective arthritides
Primary biliary sclerosis
Psoriasis
Reactive arthritides
Reiter's disease
Retinopathy
Rheumatoid arthritis
Sclerosing cholangitis
Sjögren's syndrome
Stiff-man syndrome
Subacute thyroiditis
Systemic lupus erythematosis
Systemic necrotizing vasculitides
Systemic sclerosis (scleroderma)
Takayasu's arteritis
Temporal arteritis
Thromboangiitis obliterans
Type I and type II autoimmune polyglandular syndrome
Ulcerative colitis
Uveitis
Wegener's granulomatosis As used herein, the term "ester" refers to a group of the form —COOR, wherein R is a radical notionally derived from the alcohol ROH. Examples of ester groups include the physiologically hydrolysable esters such as the methyl, ethyl, n- and iso-propyl, n-, sec- and tert-butyl, and benzyl esters.

As used herein the term "alkylene" refers to a straight or branched alkyl chain having two unsatisfied valencies, for example —$CH_2$—, —$CH_2CH_2$—, —$CH_2CH_2CH_2$—, —$CH(CH_3)CH_2$—, —$CH(CH_2CH_3)CH_2CH_2CH_3$, and —$C(CH_3)_3$.

Unless otherwise specified in the context in which it occurs, the term "substituted" as applied to any moiety herein means substituted with up to four substituents, each of which independently may be ($C_1$-$C_6$)alkyl, trifluoromethyl, ($C_1$-$C_6$) alkoxy (including the special case where a ring is substituted on adjacent ring C atoms by methylenedioxy or ethylenedioxy), trifluoromethoxy, ($C_1$-$C_6$)alkylthio, phenyl, benzyl, phenoxy, hydroxy, mercapto, amino, fluoro, chloro, bromo, cyano, nitro, oxo, —COOH, —$SO_2$OH, —$CONH_2$, —$SO_2NH_2$, —$COR^A$, —$COOR^A$, —$SO_2OR^A$, —$NHCOR^A$, —$NHSO_2R^A$, —$CONHR^A$, —$SO_2NHR^A$, —$NHR^A$, —$NR^AR^B$, —$CONR^AR^B$ or —$SO_2NR^AR^B$ wherein $R^A$ and $R^B$ are independently a ($C_1$-$C_6$)-alkyl group, a ($C_3$-$C_7$) cycloalkyl group or $C_2$-$C_6$ alkoxy group. In the case where "substituted" means substituted by benzyl or phenoxy, the phenyl ring thereof may itself be substituted with any of the foregoing, except phenyl or benzyl.

As used herein the unqualified term "carbocyclyl" or "carbocyclic" refers to a 5-8 membered ring whose ring atoms are all carbon.

Some compounds of the invention contain one or more chiral centres because of the presence of asymmetric carbon atoms. The presence of asymmetric carbon atoms gives rise to stereoisomers or diastereoisomers with R or S stereochemistry at each chiral centre. The invention includes all such stereoisomers and diastereoisomers and mixtures thereof.

Salts of salt forming compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates; and base addition salts, for example sodium, potassium, magnesium, and calcium salts.

In the compounds of the invention the following are examples of the several structural variables:

Z may be, for example a carboxylic acid group (—COOH) or a methyl or benzyl ester thereof. Presently —COOH is preferred.

$R_1$ may be, for example, H, F, Cl, methyl, methoxy, or methylenedioxy. Currently it is preferred that $R_1$ is H, F, or Cl;

$R_2$ may be, for example cyclopropyl, phenyl, or fluoro-, chloro-, methyl, methoxy-, nitro-, or amino-substituted phenyl;

$R_3$ may be, for example, H, F, Cl, methyl, methoxy, or methylenedioxy. Currently it is preferred that $R_3$ is H, F, or Cl;

Y may be, for example, —O—, —S—, or —N($R_5$)— wherein $R_5$ represents H or methyl. —NH— is presently preferred.

X may be, for example a bond, or a —$CH_2$— or —$CH_2CH_2$— radical. A bond is presently preferred.

As mentioned above, the invention includes pharmaceutical or veterinary composition comprising a compound of formula (I) or a pharmaceutically or veterinarily acceptable salt thereof together with a pharmaceutically or veterinarily acceptable excipient or carrier. In such compositions, it will be understood that the specific dose level for any particular patient will depend upon a variety of factors including the activity of the specific compound employed, the age, body weight, general health, sex, diet, time of administration, route of administration, rate of excretion, drug combination and the causative organism and severity of the particular disease undergoing therapy. Optimum dose levels and frequency of dosing will be determined by clinical trial.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

Compounds of the invention may be prepared by synthetic methods known in the literature, from compounds which are commercially available or are accessible from commercially available compounds. For example, compounds of formula (I) wherein Y is N may be prepared by reaction of a compound of formula (II) with an hydrazide of formula (III):

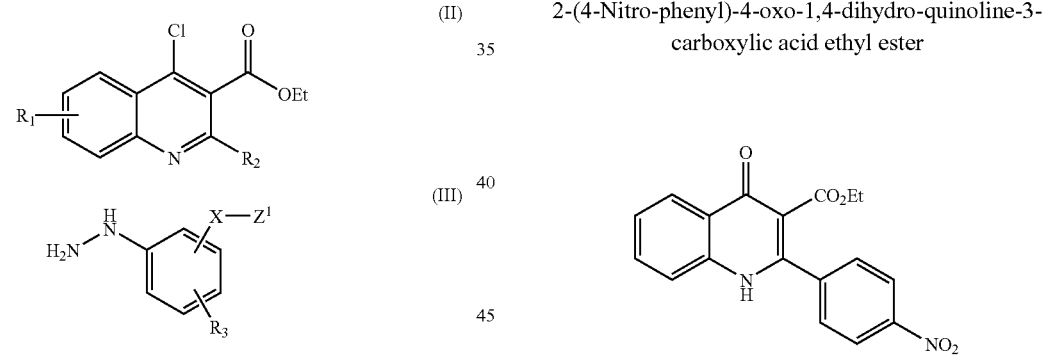

wherein Z1 is a carboxylic acid or an esterified carboxylic acid. Ester compounds (I) may of course be hydrolysed to the free acid.

The following Examples illustrate the preparation of compounds of the invention:

Synthetic Route Followed:

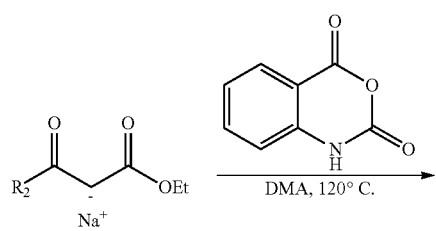

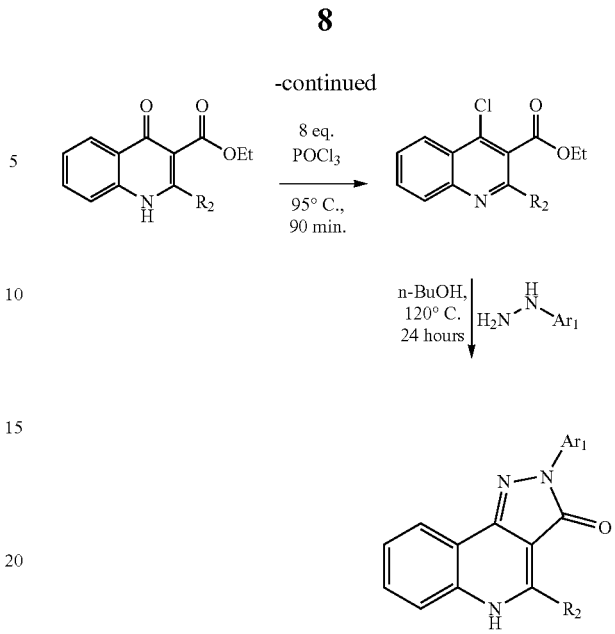

Typical experimental $R_2$=4-nitro phenyl, $Ar_1$=4-benzoic acid methyl ester

EXAMPLE 1

Step 1

2-(4-Nitro-phenyl)-4-oxo-1,4-dihydro-quinoline-3-carboxylic acid ethyl ester

Sodium hydride (0.92 g, 0.023 mol; 60% suspension in mineral oil) was added portionwise to a stirred solution of 3-(4-nitrophenyl)-3-oxopropionic acid ethyl ester (5.46 g, 0.023 mol) in dimethylacetamide (20 mL) at room temperature. A solution of isatoic anhydride (3.4 g, 0.02 mol) in dimethylacetamide (20 mL) was added to this solution. The reddish mixture was stirred at 120° C. for 30 min and then the solvent was concentrated in vacuo. The crude solid was partitioned between water and ethyl acetate and the organic phase then separated. The combined organic extracts were dried over sodium sulfate and concentrated in vacuo to leave a residue which was washed once with cold tert-butylmethyl ether to yield 2-(4-nitrophenyl)-4-oxo-1,4-dihydroquinoline-3-carboxylic acid ethyl ester (1.61 g, 28%) as a white solid, LCMS m/z 339.33 $[M+H]^+$ @ $R_T$ 1.16 min, 100% purity.

Step 2

4-Chloro-2-(4-nitro-phenyl)-quinoline-3-carboxylic acid ethyl ester

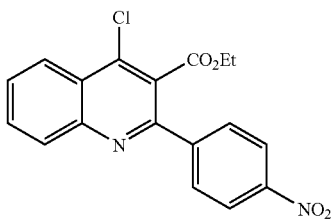

Phosphorus oxychloride (8 mL, 0.087 mol) was added in one portion to 2-(4-nitrophenyl)-4-oxo-1,4-dihydroquinoline-3-carboxylic acid ethyl ester (3.7 g, 0.0109 mol) and the mixture was heated at 95° C. for 90 min. The resulting light brown solution was added dropwise to a vigorously stirred ice-cold solution of sodium hydroxide (500 mL; 0.7 M). The aqueous suspension was extracted with ethyl acetate and the combined organic extracts were dried and concentrated in vacuo to leave 4-chloro-2-(4-nitophenyl)-quinoline-3-carboxylic acid ethyl ester (3.8 g, 98%) as a white solid, LCMS m/z 357.21 [M+H]$^+$ @ R$_T$ 1.94 min, 98% purity.

Step 3

4-[4-(4-Nitro-phenyl)-3-oxo-3,5-dihydro-pyrazolo[4,3-c]quinolin-2-yl]-benzoic acid methyl ester

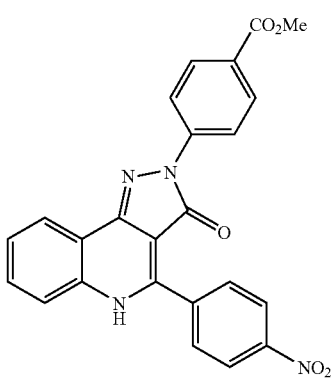

4-Chloro-2-(4-nitrophenyl)-quinoline-3-carboxylic acid ethyl ester (2.86 g, 0.008 mol) and 4-hydrazino-benzoic acid methyl ester hydrochloride (1.7 g, 0.008 mol) were stirred in n-butanol (70 mL) at 120° C. for 24 h. The bright orange suspension was diluted with tert-butylmethyl ether, filtered, washed with cold heptane and left to dry under suction to yield 4-[4-(4-nitrophenyl)-3-oxo-3,5-dihydropyrazolo[4,3-c]quinolin-2-yl]-benzoic acid methyl ester (2.7 g, 76%) as an orange solid, LCMS m/z 441.35 [M+H]$^+$ @ R$_T$ 1.66 min: 84% purity.

EXAMPLE 2

4-[4-(4-Amino-phenyl)-3-oxo-3,5-dihydro-pyrazolo[4,3-c]quinolin-2-yl]-benzoic acid methyl ester

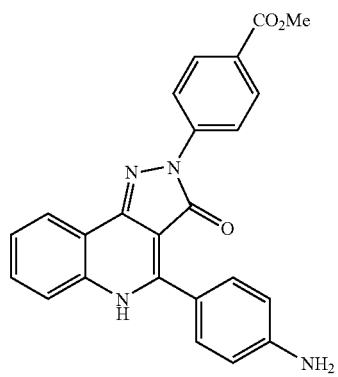

4-[4-(4-Nitro-phenyl)-3-oxo-3,5-dihydro-pyrazolo[4,3-c]quinolin-2-yl]-benzoic acid methyl ester (2.6 g, 5.9 mmol) and Pd/C (100 mg, 10%) were suspended in ethanol (150 mL) and acetic acid (6 mL) and stirred under hydrogen for 24 h. The resulting yellow-orange suspension was diluted with DMF (50 mL) and filtered. The solvent was removed in vacuo to leave a residue which was washed with methanol to give 4-[4-(4-amino-phenyl)-3-oxo-3,5-dihydro-pyrazolo[4,3-c]quinolin-2-yl]-benzoic acid methyl ester (2.0 g, 82%) as a pale orange solid, LCMS m/z 411.39 [M+H]$^+$ @ R$_T$ 1.27 min, 79% purity.

EXAMPLE 3

4-[4-(4-Nitro-phenyl)-3-oxo-3,5-dihydro-pyrazolo[4,3-c]quinolin-2-yl]-benzoic acid

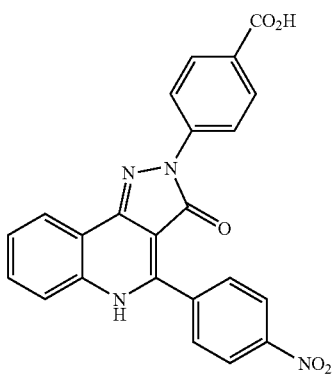

Prepared using the procedure described above, using 4-hydrazinobenzoic acid. LCMS m/z 427.34 [M+H]$^+$ @ R$_T$ 1.38 min, 74% purity

EXAMPLE 4

3-[4-(4-Nitro-phenyl)-3-oxo-3,5-dihydro-pyrazolo[4,3-c]quinolin-2-yl]-benzoic acid

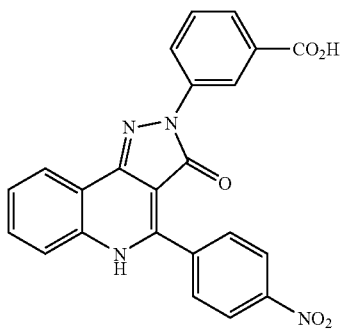

Prepared by methods analogous to Example 3. LCMS m/z 427.37 [M+H]$^+$ @ R$_T$ 1.28 min, 96% purity.

EXAMPLE 5

4-[4-(3-Nitro-phenyl)-3-oxo-3,5-dihydro-pyrazolo[4,3-c]-quinolin-2-yl]-benzoic acid

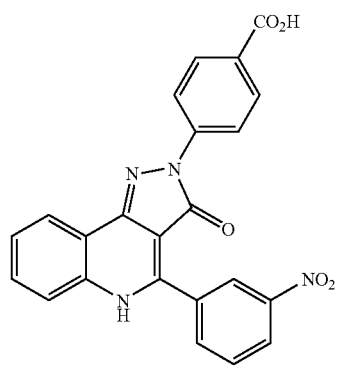

Prepared by methods analogous to Example 3. LCMS m/z 427.38 [M+H]$^+$ @ R$_T$ 1.33 min, 88% purity. δ$_H$(400 MHz, (CD$_3$)$_2$SO) 12.8 (1H, s), 8.85 (1H, t J 2.0), 8.54 (1H, dd J$_1$ 7.1 J$_2$ 2.0), 8.35 (4H, m), 8.02 (1H, s), 8.0 (1H, s), 7.94 (1H, t J 8.0), 7.84 (1H, d J 7.9), 7.74 (1H, t, J 7.1), 7.6 (1H, t J 7.1).

EXAMPLE 6

4-[4-(4-Methoxyphenyl)-3-oxo-3,5-dihydropyrazolo[4,3-c]quinolin-2-yl]benzoic acid methyl ester

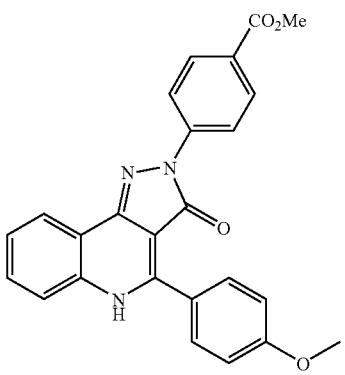

Prepared by methods analogous to Example 1. LCMS m/z 426.34 [M+H]$^+$ @ R$_T$ 1.71 min, 82% purity. δ$_H$(400 MHz, (CD$_3$)$_2$SO) 8.2 (2H, d J 9.0), 8.05 (1H, dd J$_1$ 8.0 J$_2$ 1.1), 7.82 (2H, d J 9.0), 7.77 (2H, d J 9.0), 7.65 (1H, d J 9.0), 7.48 (1H, td J$_1$ 8.2 J$_2$ 1.3), 7.34 (1H, td J$_1$ 7.0 J$_2$ 1.1), 6.98 (2H, d J 9.0).

EXAMPLE 7

4-[4-(4-Methoxyphenyl)-3-oxo-3,5-dihydropyrazolo[4,3-c]-quinolin-2-yl]benzoic acid

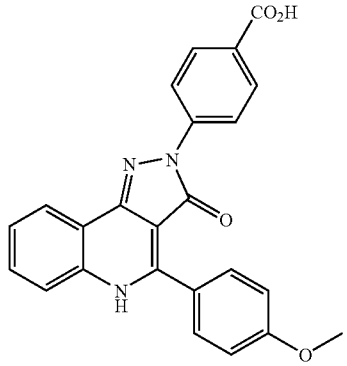

Prepared using the procedure analogous to Example 1. LCMS m/z 412.28 [M+H]$^+$ @ R$_T$ 1.28 min, 88% purity.

EXAMPLE 8

4-[4-(4-Aminophenyl)-3-oxo-3,5-dihydropyrazolo[4,3-c]-quinolin-2-yl]benzoic acid methyl ester

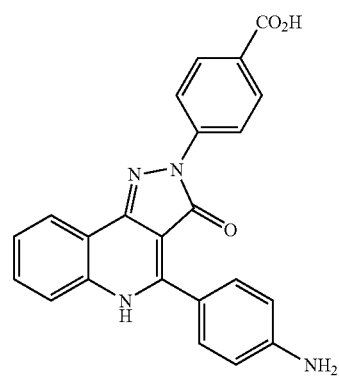

Prepared using the procedure analogous to Example 1. LCMS m/z 397.36 [M+H]$^+$ @ R$_T$ 1.11 min, 63% purity.

EXAMPLE 9

3-[4-(4-Methoxyphenyl)-3-oxo-3,5-dihydropyrazolo[4,3-c]-quinolin-2-yl]benzoic acid methyl ester

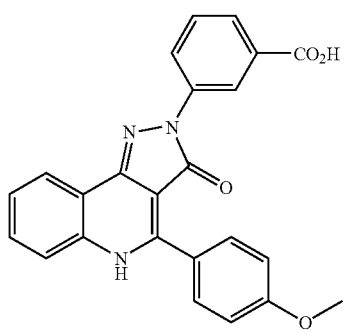

Prepared using the procedure analogous to Example 1, using 3-hydrazinobenzoic acid. LCMS m/z 412.3 [M+H]$^+$ @ R$_T$ 1.29 min, 86% purity.

EXAMPLE 10

4-[4-(3-Nitrophenyl)-3-oxo-3,5-dihydropyrazolo[4,3-c]-quinolin-2-yl]benzoic acid methyl ester

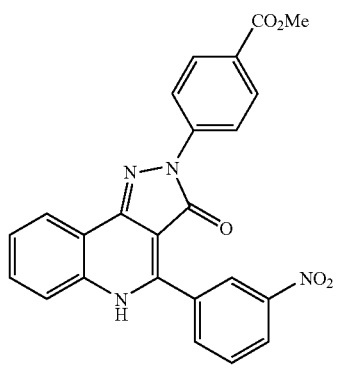

Prepared by methods analogous to Example 1. LCMS m/z 441.37 [M+H]$^+$ @ R$_T$ 1.80 min, 82% purity.

EXAMPLE 11

4-[3-Oxo-4-(2,4,5-trifluorophenyl)-3,5-dihydropyrazolo-[4,3-c]quinolin-2-yl]benzoic acid

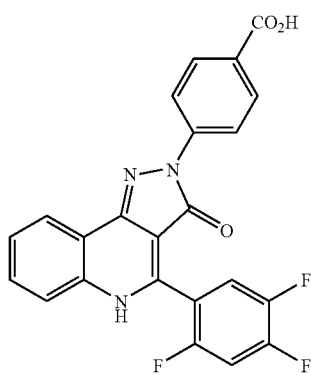

Prepared by methods analogous to Example 3. LCMS m/z 436.36 [M+H]$^+$ @ R$_T$ 1.30 min, 83% purity.

BIOLOGICAL EXAMPLE

The examples described above were tested in a cell free Homogenous Time Resolved Fluorescence (HTRF) assay to determine their activity as inhibitors of the CD80-CD 28 interaction.

In the assay, europium and allophycocyanin (APC) are associated with CD28 and CD80 indirectly (through antibody linkers) to form a complex, which brings the europium and APC into close proximity to generate a signal. The complex comprises the following six proteins: fluorescent label 1, linker antibody 1, CD28 fusion protein, CD80 fusion protein, linker antibody 2, and fluorescent label 2. The table below describes these reagents in greater detail.

| | |
|---|---|
| Fluorescent label 1 | Anti-Rabbit IgG labelled with Europium (1 μg/ml) |
| Linker antibody 1 | Rabbit IgG specific for mouse Fc fragment (3 μg/ml) |
| CD28 fusion protein | CD28 - mouse Fc fragment fusion protein (0.48 μg/ml) |
| CD80 fusion protein | CD80 mouse Fab fragment (C215) fusion protein (1.9 μg/ml) |
| Linker antibody 2 | GαMκ-biotin: biotinylated goat IgG specific for mouse kappa chain (2 μg/ml) |
| Fluorescent label 2 | SA-APC: streptavidin labelled allophycocyanin (8 μg/ml) |

On formation of the complex, europium and APC are brought into proximity and a signal is generated.

Non-specific interaction was measured by substituting a mouse Fab fragment (C215) for the CD80 mouse Fab fragment fusion protein (1.9 μg/ml). The assay was carried out in black 384 well plates in a final volume of 30 μl. Assay buffer: 50 mM Tris-HCl, 150 mM NaCl pH7.8, containing 0.1% BSA (w/v) added just prior to use.

Compounds were added to the above reagents in a concentration series ranging between 100 μM-1.7 nM. The reaction was incubated for 4 hours at room temperature. Dual measurements were made using a Wallac Victor 1420 Multilabel Counter. First measurement: excitation 340 nm, emission 665 nm, delay 50 μs, window time 200 μs. second measurement: excitation 340 nm, emission 615 nm, delay 50 μs, window time 200 μs. Counts were automatically corrected for fluorescence crossover, quenching and background.

By way of illustration, the IC$_{50}$ results for the compounds of Examples 5, 7 and 9 were 8.6 μM, 3.4 μM and 4.6 μM respectively.

The invention claimed is:

1. A compound of formula (I) or a pharmaceutically or veterinarily acceptable salt thereof:

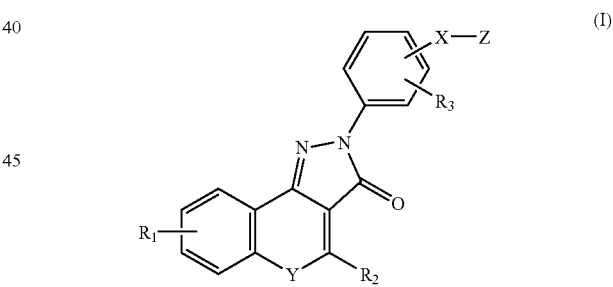

wherein

Z represents a carboxylic acid group (—COOH) or an ester thereof;

R$_1$ and R$_3$ independently represent H; F; Cl; Br; —NO$_2$; —CN; C$_1$-C$_6$ alkyl optionally substituted by F or Cl; or C$_1$-C$_6$ alkoxy optionally substituted by F;

R$_2$ represents optionally substituted C$_7$ cycloalkyl, substituted C$_3$-C$_7$ cycloalkyl or optionally substituted phenyl;

Y represents N-oxide or —N(R$_5$)— wherein R$_5$ represents H or C$_1$-C$_6$ alkyl; and X represents a bond or a group selected from; a divalent C$_1$-C$_6$ alkylene radical, NHC(O)C$_{1-5}$ alkyl or NHC(O)CH$_2$—O—CH$_2$.

2. The compound of claim 1 wherein X is a bond or a —CH$_2$— or —CH$_2$CH$_2$-radical.

3. The compound of claim 1 wherein Z is —COOH.

4. The compound of claim 1 wherein $R_1$ is H, F, Cl, methyl, methoxy, or methylenedioxy.

5. The compound of claim 1 wherein $R_2$ is cyclopropyl, phenyl, or fluoro-, chloro-, methyl, methoxy-, nitro-, or amino-substituted phenyl.

6. The compound of claim 1 wherein $R_3$ is H, F, Cl, methyl, methoxy, or methylenedioxy.

7. The compound of claim 1 wherein Y is —N($R_5$)— wherein $R_5$ represents H or methyl.

8. A pharmaceutical or veterinary composition comprising a compound of claim 1 together with a pharmaceutically or veterinarily acceptable excipient or carrier.

9. The compound of claim 2 wherein Z is —COOH.

10. The compound of claim 2 wherein $R_1$ is H, F, Cl, methyl, methoxy, or methylenedioxy.

11. The compound of claim 2 wherein $R_2$ is cyclopropyl, phenyl, or fluoro-, chloro-, methyl, methoxy-, nitro-, or amino-substituted phenyl.

12. The compound of claim 2 wherein $R_3$ is H, F, Cl, methyl, methoxy, or methylenedioxy.

13. The compound of claim 2 wherein Y is —N($R_5$)— wherein $R_5$ represents H or methyl.

14. A pharmaceutical or veterinary composition comprising the compound of claim 2 together with a pharmaceutically or veterinarily acceptable excipient or carrier.

15. A pharmaceutical or veterinary composition comprising the compound as claimed in claim 3 together with a pharmaceutically or veterinarily acceptable excipient or carrier.

16. A pharmaceutical or veterinary composition comprising the compound of claim 4 together with a pharmaceutically or veterinarily acceptable excipient or carrier.

* * * * *

UNITED STATES PATENT AND TRADEMARK OFFICE
CERTIFICATE OF CORRECTION

PATENT NO.        : 7,674,906 B2                                                    Page 1 of 1
APPLICATION NO.   : 10/537538
DATED             : March 9, 2010
INVENTOR(S)       : Ian Richard Matthews It is certified that error appears in the above-identified patent and that said Letters Patent is hereby corrected as shown below:

Title Page

At (*) of Col. 1 insert:

--This patent is subject to a terminal disclaimer.--

Signed and Sealed this

Twenty-second Day of June, 2010

David J. Kappos
*Director of the United States Patent and Trademark Office*